(12) United States Patent
Kim et al.

(10) Patent No.: US 10,080,550 B2
(45) Date of Patent: Sep. 25, 2018

(54) ULTRASONIC APPARATUS AND CONTROL METHOD FOR THE SAME

(71) Applicant: SAMSUNG ELECTRONICS CO., LTD., Suwon-si (KR)

(72) Inventors: Baehyung Kim, Yongin-si (KR); Youngil Kim, Suwon-si (KR); Jong Keun Song, Yongin-si (KR); Seungheun Lee, Seongnam-si (KR); Taeho Jeon, Seoul (KR); Kyungil Cho, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 165 days.

(21) Appl. No.: 14/684,497

(22) Filed: Apr. 13, 2015

(65) Prior Publication Data
US 2015/0293062 A1    Oct. 15, 2015

(30) Foreign Application Priority Data

Apr. 15, 2014 (KR) .................. 10-2014-0044638

(51) Int. Cl.
| | |
|---|---|
| *A61B 8/00* | (2006.01) |
| *G01N 29/07* | (2006.01) |
| *A61B 8/13* | (2006.01) |
| *A61B 8/08* | (2006.01) |
| *G01S 15/89* | (2006.01) |
| *G01S 7/52* | (2006.01) |

(52) U.S. Cl.
CPC ........ *A61B 8/5253* (2013.01); *G01S 7/52036* (2013.01); *G01S 7/52049* (2013.01); *G01S 7/52071* (2013.01); *G01S 15/8915* (2013.01); *G01S 15/8993* (2013.01); *G01S 15/8995* (2013.01); *A61B 8/4483* (2013.01)

(58) Field of Classification Search
CPC ............. G01S 15/8993; G01S 15/8995; G01S 15/8915; G01S 15/8952; G01S 7/52049; G01S 7/52036; G01S 7/52071; A61B 8/5253

See application file for complete search history.

(56) References Cited

U.S. PATENT DOCUMENTS 4,649,927 A * 3/1987 Fehr .................... G01S 7/52065
348/163
4,700,571 A * 10/1987 Okazaki .................. G01H 5/00
73/597

(Continued)

FOREIGN PATENT DOCUMENTS

| KR | 10-1138571 B1 | 5/2012 |
| KR | 10-1202510 B1 | 11/2012 |
| KR | 10-1246974 B1 | 3/2013 |

*Primary Examiner* — Helen Kwok
(74) *Attorney, Agent, or Firm* — Sughrue Mion, PLLC

(57) ABSTRACT

Disclosed herein are an ultrasonic apparatus for imaging an ultrasonic signal and a control method for the same. The ultrasonic apparatus may include a transducer configured to irradiate a plurality of ultrasonic waves which have different traveling directions onto an object and to collect a plurality of echo ultrasonic waves reflected from the object; and a controller configured to acquire a plurality of sound velocities of the plurality of ultrasonic waves in the object and to compound the acquired plurality of sound velocities in order to determine a composite sound velocity in the object.

17 Claims, 19 Drawing Sheets

(56) References Cited

U.S. PATENT DOCUMENTS

| | | | |
|---|---|---|---|
| 4,779,623 A * | 10/1988 | Sumino | A61B 8/0858 600/440 |
| 5,143,070 A | 9/1992 | Ophir et al. | |
| 5,181,778 A | 1/1993 | Beller | |
| 5,381,693 A * | 1/1995 | Kobayashi | G01N 29/0609 600/441 |
| 5,415,173 A * | 5/1995 | Miwa | G01S 7/52049 600/447 |
| 5,755,228 A | 5/1998 | Wilson et al. | |
| 5,908,390 A * | 6/1999 | Matsushima | G01S 7/52023 600/447 |
| 6,117,081 A * | 9/2000 | Jago | G01S 7/52025 600/443 |
| 6,210,328 B1 * | 4/2001 | Robinson | G01S 7/52025 600/437 |
| 6,309,352 B1 | 10/2001 | Oraevsky et al. | |
| 6,530,885 B1 * | 3/2003 | Entrekin | G01S 7/52053 128/916 |
| 7,836,766 B2 * | 11/2010 | Jeong | A61B 8/5269 600/447 |
| 8,708,910 B2 * | 4/2014 | Katsuyama | A61B 8/14 600/407 |
| 2003/0010124 A1 * | 1/2003 | Bates | G01N 25/72 73/606 |
| 2003/0036706 A1 | 2/2003 | Slayton et al. | |
| 2003/0092989 A1 * | 5/2003 | Aichhorn | A61B 8/08 600/443 |
| 2003/0092990 A1 * | 5/2003 | Baba | A61B 8/00 600/443 |
| 2003/0171672 A1 | 9/2003 | Varghese et al. | |
| 2004/0210137 A1 * | 10/2004 | Baba | G01S 7/52034 600/443 |
| 2007/0167801 A1 * | 7/2007 | Webler | G06F 19/3437 600/459 |
| 2007/0239020 A1 * | 10/2007 | Iinuma | A61B 8/0825 600/459 |
| 2008/0058682 A1 | 3/2008 | Azhari et al. | |
| 2008/0097207 A1 | 4/2008 | Cai | |
| 2008/0242999 A1 * | 10/2008 | Kakee | A61B 8/00 600/458 |
| 2009/0003128 A1 * | 1/2009 | Jeong | A61B 8/5269 367/7 |
| 2009/0099451 A1 * | 4/2009 | Nakaya | G01S 7/52046 600/443 |
| 2010/0020080 A1 * | 1/2010 | Iwanaga | G06T 15/60 345/426 |
| 2010/0076312 A1 * | 3/2010 | Katsuyama | A61B 8/00 600/443 |
| 2010/0217162 A1 | 8/2010 | Hissong et al. | |
| 2011/0054318 A1 * | 3/2011 | Shin | A61B 5/489 600/443 |
| 2011/0060221 A1 | 3/2011 | Fan et al. | |
| 2011/0098565 A1 * | 4/2011 | Masuzawa | G01S 7/52047 600/443 |
| 2011/0166807 A1 * | 7/2011 | Kitazawa | G01N 29/0663 702/56 |
| 2012/0004551 A1 * | 1/2012 | Katsuyama | A61B 8/14 600/443 |
| 2012/0011935 A1 * | 1/2012 | Kim | G01S 7/52049 73/597 |
| 2012/0078105 A1 * | 3/2012 | Kamiyama | A61B 8/5207 600/447 |
| 2012/0310093 A1 * | 12/2012 | Tanabe | G01S 7/52049 600/443 |
| 2013/0012819 A1 | 1/2013 | Haugen et al. | |
| 2013/0041262 A1 * | 2/2013 | Katsuyama | G01S 7/52049 600/447 |
| 2013/0116564 A1 * | 5/2013 | Katsuyama | A61B 8/469 600/442 |
| 2013/0123628 A1 * | 5/2013 | Katsuyama | A61B 6/469 600/442 |
| 2013/0190625 A1 * | 7/2013 | Shibamoto | A61B 8/546 600/447 |
| 2014/0031689 A1 * | 1/2014 | Kang | G01S 15/8977 600/443 |
| 2014/0187953 A1 * | 7/2014 | Miyachi | G01S 7/52049 600/447 |
| 2015/0049582 A1 * | 2/2015 | Miyachi | A61B 8/4483 367/7 |
| 2015/0057542 A1 * | 2/2015 | Katsuyama | A61B 8/5207 600/438 |
| 2015/0080734 A1 * | 3/2015 | Katsuyama | A61B 8/469 600/447 |
| 2015/0196274 A1 * | 7/2015 | Yamamoto | A61B 8/485 600/442 |
| 2015/0198566 A1 * | 7/2015 | Yamamoto | A61B 8/00 73/597 |
| 2015/0201909 A1 * | 7/2015 | Yamamoto | A61B 8/4461 600/442 |
| 2015/0289837 A1 * | 10/2015 | Kim | A61B 8/4455 600/454 |
| 2015/0309173 A1 * | 10/2015 | Shiba | G01H 5/00 367/100 |
| 2017/0000463 A1 * | 1/2017 | Fujii | A61B 8/5269 |

\* cited by examiner

ULTRASONIC APPARATUS AND CONTROL METHOD FOR THE SAME

CROSS-REFERENCE TO RELATED APPLICATION

This application claims priority from Korean Patent Application No. 10-2014-44638, filed on Apr. 15, 2014 in the Korean Intellectual Property Office, the disclosure of which is incorporated herein by reference in its entirety.

BACKGROUND

1. Field

Exemplary embodiments relate to an ultrasonic apparatus for imaging an ultrasonic signal and a control method for the same.

2. Description of the Related Art

Ultrasonic diagnostic apparatuses direct ultrasonic signals from a body surface of a subject to a desired region inside a human body, and obtain an image related to a mono layer of soft tissue or a blood-flow using the ultrasonic signals reflected from the desired region, i.e., obtain information of the ultrasonic echo signals in a non-invasive manner.

In general, ultrasonic diagnostic apparatuses have a small size, a low price, a real-time displaying function, and high safety because of no exposure to radiation, such as X-ray radiation. Thus, ultrasonic diagnostic apparatuses are widely used for diagnosis of cardiac disease, breast disease, abdominal disease, urinary system disease, obstetric and gynecologic disease, and so on.

However, ultrasonic diagnostic apparatuses generate ultrasonic images using only magnitudes of reflected ultrasonic signals, and therefore, it is difficult to check detailed characteristics of a medium into which an ultrasonic wave is directed. Therefore, recently, an ultrasonic functional image, which is an ultrasonic image which relates to parameters such as elasticity, attenuation, and sound velocity, has been also used in addition to a general ultrasonic image.

SUMMARY

The ultrasonic apparatus is designed on the assumption that a sound velocity of an irradiated ultrasonic wave in a medium is known. This is because a delay due to a difference in a traveling distance may be considered when the reflected ultrasonic signal is focused. When each ultrasonic signal is delayed based on the delay due to the difference in the traveling distance, the reflected ultrasonic signal has the same phase, thus maximizing the amplitude of the ultrasonic signal when focused.

Accordingly, an ultrasonic apparatus that irradiates a plurality of ultrasonic waves having different respective traveling directions onto an object and compounds the acquired sound velocities in order to determine a composite sound velocity and a control method for the same are provided in order to acquire an accurate sound velocity.

In accordance with one aspect of one or more exemplary embodiments, an ultrasonic apparatus includes a transducer configured to irradiate a plurality of ultrasonic waves which have different respective traveling directions onto an object and to collect a plurality of echo ultrasonic waves reflected from the object, and a controller configured to acquire a plurality of sound velocities of the plurality of ultrasonic waves in the object and to compound the acquired plurality of sound velocities in order to determine a composite sound velocity in the object.

In accordance with another aspect of one or more exemplary embodiments, an ultrasonic apparatus includes a transducer configured to irradiate a plurality of ultrasonic waves which have different respective traveling directions onto an object and to collect a plurality of echo ultrasonic waves, a controller configured to acquire a plurality of respective sound velocities of the plurality of ultrasonic waves in the object and to compound the acquired plurality of sound velocities in order to determine a composite sound velocity in the object, and a beamformer configured to delay the collected echo ultrasonic waves based on the determined composite sound velocity, to focus the delayed echo ultrasonic waves, and to convert the focused echo ultrasonic waves into respective ultrasonic image signals.

In accordance with still another aspect of one or more exemplary embodiments, an ultrasonic apparatus includes a transducer configured to irradiate a plurality of ultrasonic waves which have different respective traveling directions onto an object and to collect a plurality of echo ultrasonic waves reflected from the object, a controller configured to acquire a plurality of respective sound velocities of the plurality of ultrasonic waves in the object and to compound the acquired plurality of sound velocities in order to determine a composite sound velocity in the object, and a thermal image generator configured to generate a thermal image of the object based on the determined composite sound velocity.

In accordance with one aspect of one or more exemplary embodiments, a method for controlling an ultrasonic apparatus is provided. The method includes irradiating a plurality of ultrasonic waves which have different respective traveling directions onto an object, collecting a plurality of echo ultrasonic waves reflected from the object, acquiring a plurality of respective sound velocities of the plurality of ultrasonic waves in the object; and compounding the acquired plurality of sound velocities in order to determine a composite sound velocity in the object.

In accordance with another aspect of one or more exemplary embodiments, a method for controlling an ultrasonic apparatus is provided. The method includes irradiating a plurality of ultrasonic waves which have different traveling directions onto an object, acquiring a plurality of respective sound velocities of the plurality of ultrasonic waves, compounding the plurality of sound velocities in order to determine a composite sound velocity in the object; and delaying the echo ultrasonic waves based on the determined composite sound velocity, focusing the delayed echo ultrasonic waves, and converting the focused echo ultrasonic waves into respective ultrasonic image signals.

In accordance with still another aspect of one or more exemplary embodiments, a method for controlling an ultrasonic apparatus is provided. The method includes irradiating a plurality of ultrasonic waves which have different respective traveling directions onto an object, acquiring a plurality of respective sound velocities of the plurality of ultrasonic waves, compounding the plurality of sound velocities in order to determine a composite sound velocity in the object; and generating a thermal image of the object based on the determined composite sound velocity.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
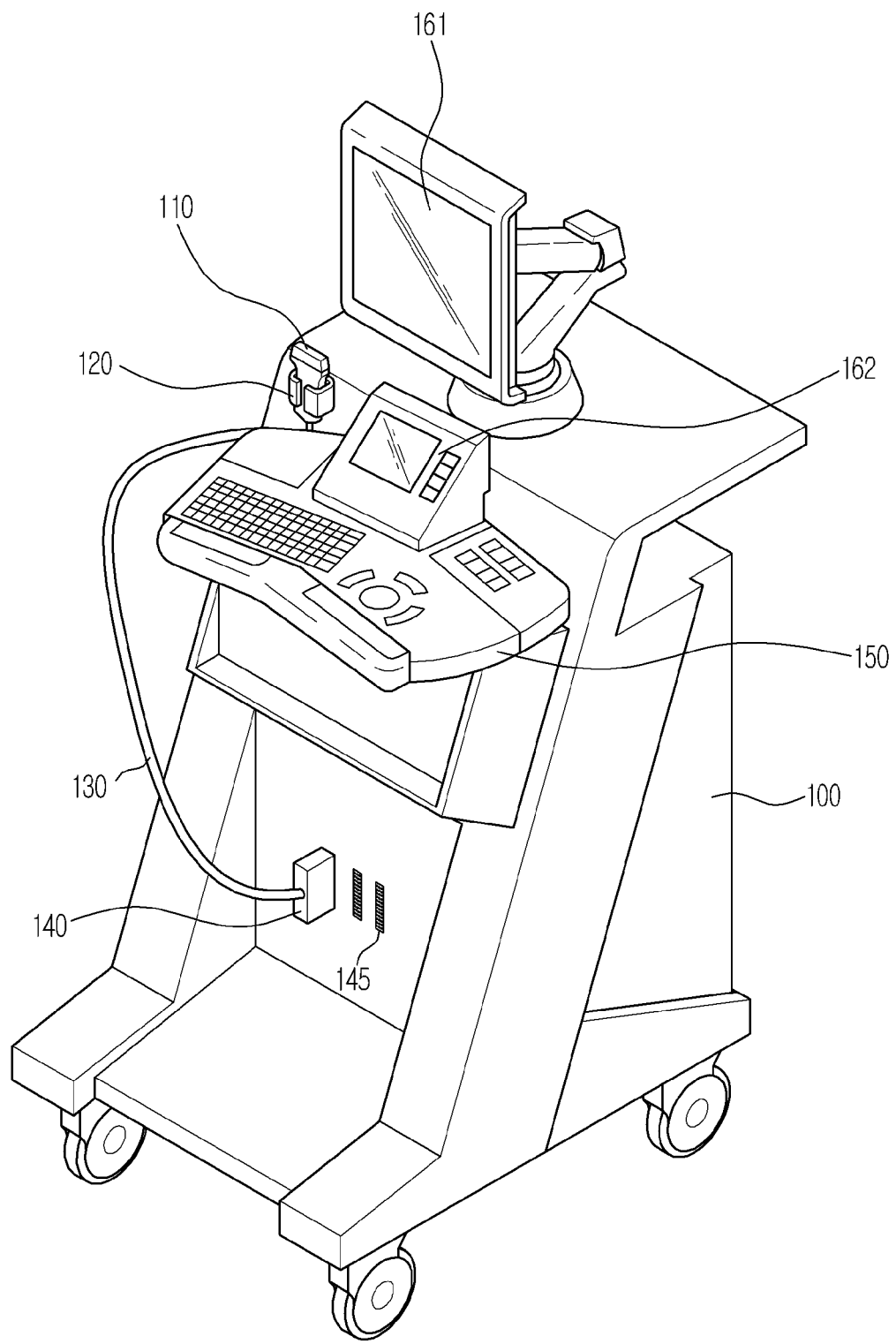
FIG. 1 is a perspective view showing an ultrasonic apparatus, according to an exemplary embodiment.

Reference will now be made in detail to the exemplary embodiments, examples of which are illustrated in the accompanying drawings, wherein like reference numerals refer to like elements throughout.

Hereinafter, an ultrasonic apparatus and a control method for the same according to an exemplary embodiment will be described in detail with reference to the accompanying drawings.

FIG. 1 is a perspective view showing an ultrasonic apparatus, according to an exemplary embodiment. As shown in FIG. 1, the ultrasonic apparatus may include a main body 100, an ultrasonic probe 110, an input unit (also referred to herein as an "input device") 150, a main display 161, and a sub display 162.

The main body 100 may be provided with at least one female connector 145 at one side. A male connector 140 connected to a cable 130 may be physically coupled to the female connector 145.

Further, the main body 100 may be provided with a plurality of casters on a lower portion thereof in order to facilitate movement of the ultrasonic apparatus. The casters may be used to fix the ultrasonic apparatus to a predetermined position and/or to move the ultrasonic apparatus in a predetermined direction.

The ultrasonic probe 110 forms a contact with a body surface of a subject and may be configured to transmit and/or receive an ultrasonic wave. Specifically, the ultrasonic probe 110 transmits a transmission signal, i.e. an ultrasonic signal, which is provided from the main body 100, inside a body surface of a subject, receives an ultrasonic echo signal reflected from a specific portion inside the human body of the subject, and transmits the received ultrasonic echo signal to the main body 100. The cable 130 may have one end connected to the ultrasonic probe 110 and the opposite end connected to the male connector 140. The male connector 140 connected to the opposite end of the cable 130 may be physically coupled to the female connector 145 of the main body 100.

Figure 2A:
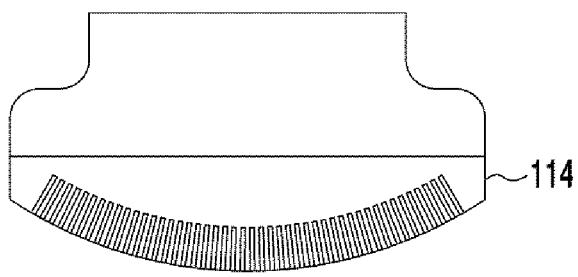
FIG. 2A is a convex array probe, according to an exemplary embodiment.
Figure 2B:
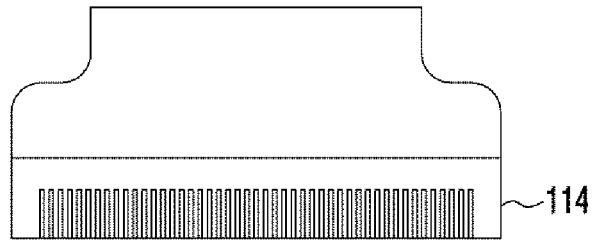
FIG. 2B is a linear array probe, according to an exemplary embodiment.

Types of the ultrasonic probe will be described with reference to FIGS. 2A and 2B. FIG. 2A is a convex array probe, according to an exemplary embodiment, and FIG. 2B is a linear array probe, according to an exemplary embodiment. One or more transducer elements which are configured for irradiating and collecting an ultrasonic wave may be provided at a front end of the ultrasonic probe 110. The type of the ultrasonic probe 110 may be classified according to a shape of an array of the transducer elements.

Referring to FIG. 2A, the convex array probe may have transducer elements 114 that are arranged in a curved line and transmit, and may be configured to receive an ultrasonic wave through a curved surface. The convex array probe is mainly used for abdominal diagnosis in obstetrics and gynecology (OB/GYN) and may be useful for a wide range of possible diagnoses with respect to a deep body part.

Conversely, the linear array probe shown in FIG. 2B has transducer elements 114 that are arranged in a straight line, and thus is configured to transmit and receive an ultrasonic wave directly forward. The linear array probe may be implemented as a high resolution probe, because the linear array probe is mainly used to inspect a breast, thyroid gland, blood vessel system, or any other part which is relatively close to the skin.

The above-described ultrasonic probe 110, which is used for the ultrasonic apparatus and the control method for the same, is merely one example of this exemplary embodiment, but not limited to the above examples. Accordingly, in an ultrasonic apparatus and a control method for the same according to another exemplary embodiment, the ultrasonic probe may be a two-dimensional (2D) array probe.

Referring back to FIG. 1, the input unit 150 is configured to receive a command associated with an operation of the ultrasonic apparatus. For example, the input unit 150 may receive a command for selecting a mode(s), such as an amplitude mode (A-mode), a brightness mode (B-mode), and/or a motion mode (M-mode) or a start command for an ultrasonic diagnosis. The command received via the input unit 150 may be transmitted to the main body 100 over wired or wireless communication.

The input unit 150 may include, for example, at least one of a keyboard, a foot switch, and a foot pedal. The keyboard may be implemented as hardware and positioned on an upper portion of the main body 100. The keyboard may include at least one of a switch, a key, a joystick, and a track ball. Alternatively, the keyboard may be implemented as software, such as, for example, a graphical user interface. In this regard, the keyboard may be displayed on the main display 161 and/or the sub display 162. The foot switch or foot pedal may be disposed at a lower portion of the main body 100. The user may control an operation of the ultrasonic apparatus by using the foot pedal.

An ultrasonic probe holder 120 for holding the ultrasonic probe 110 may be disposed in relatively close proximity to the input unit 150. The ultrasonic probe holder 120 may be provided in a plural number. The user may place and contain the ultrasonic probe 110 in the ultrasonic probe holder 120 while the ultrasonic apparatus is not in use.

A display 160 may include the main display 161 and the sub display 162.

The sub display 162 may be disposed at the main body 100. FIG. 1 illustrates that the sub display 162 is disposed on the input unit 150. The sub display 162 may display an application associated with an operation of the ultrasonic apparatus. For example, the sub display 162 may display a menu and/or an instruction required for determining an ultrasonic diagnosis. The sub display 162 may include a cathode ray tube (CRT), a liquid crystal display (LCD), or the like.

The main display 161 may be disposed at the main body 100. In FIG. 1, the main display 161 is disposed over the sub display 162. The main display 161 may display an ultrasonic image acquired during the ultrasonic diagnosis. The main display 161 may include a CRT, an LCD, or the like in the same manner as the sub display 162. FIG. 1 illustrates that the main display 161 is coupled to the main body 100. However, the main display 161 may be detachably disposed on the main body 100.

In FIG. 1, the ultrasonic apparatus is provided with both the main display 161 and the sub display 162. However, the sub display 162 may be omitted if necessary. In this case, the application or menu displayed on the sub display 162 may be displayed on the main display 161.

Figure 3:
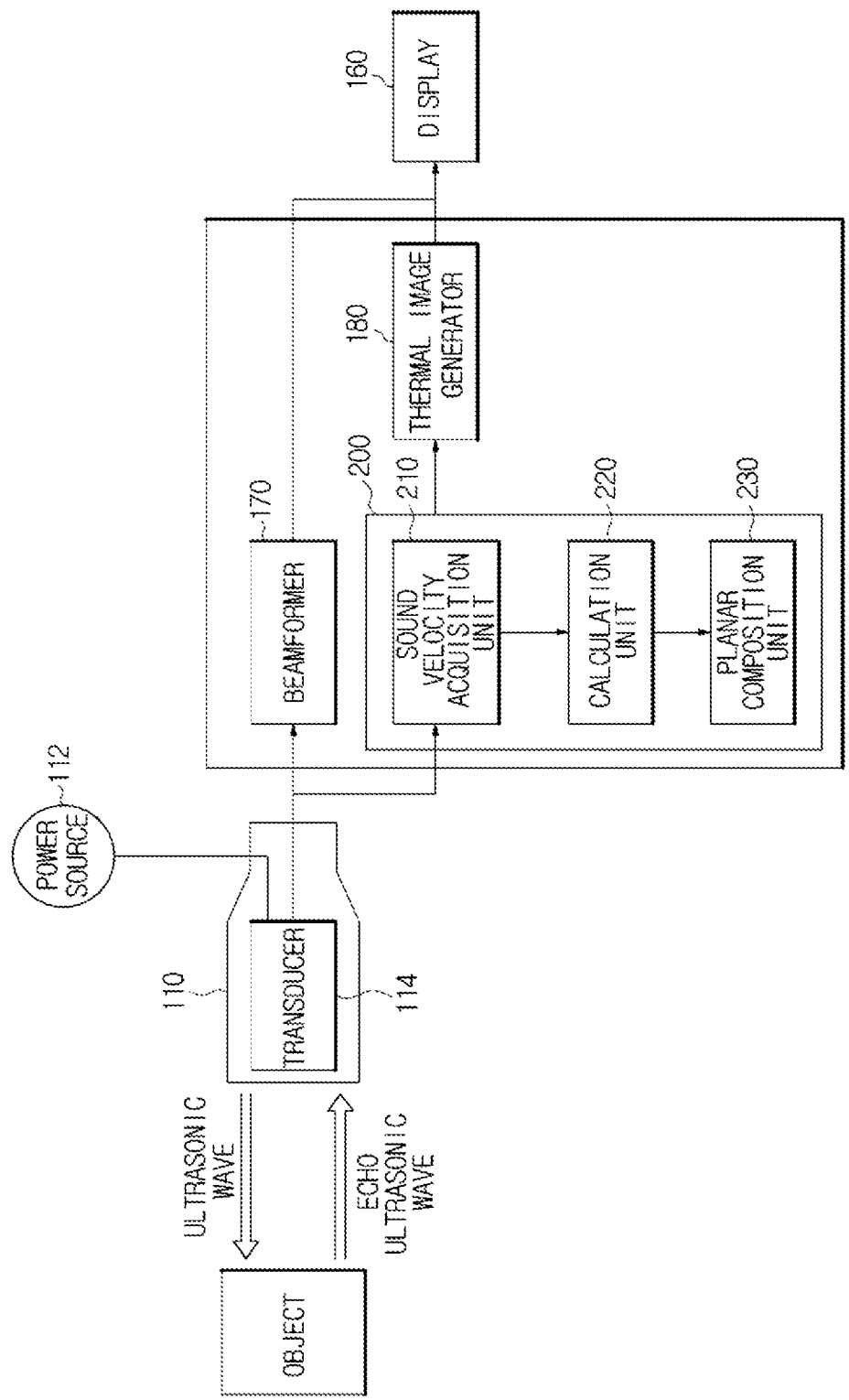
FIG. 3 is a block diagram showing a control configuration of an ultrasonic apparatus, according to an exemplary embodiment.

FIG. 3 is a block diagram showing a control configuration of an ultrasonic apparatus according to an embodiment of the present invention.

The ultrasonic probe 110 is provided with a plurality of transducers 114. The transducers 114 may be configured to generate an ultrasonic pulse according to an alternating current applied from a power source 112, to irradiate the ultrasonic pulse onto an object, to receive an echo ultrasonic wave reflected from a targeted part inside the object, and to convert the received echo ultrasonic wave into an ultrasonic echo signal, which is an electrical signal. In particular, the power source 112 may be an external power supply or an electrical storage device inside the ultrasonic apparatus.

Each of the transducers 114 may include any one or more of a magnetostrictive ultrasonic transducer using magnetostriction of a magnetic material, a piezoelectric ultrasonic transducer using the piezoelectric effect of a piezoelectric material, and a capacitive micro-machined ultrasonic transducer (hereinafter simply referred to as cMUT) which is configured for transmitting and receiving an ultrasonic wave by using vibrations of hundreds or thousands of microprocessed thin films.

As described above, the ultrasonic probe 110 may have different types, depending on a form of an arrangement of the transducers 114.

When an alternating current is applied from the power source to the transducer 114, a piezoelectric vibrator or a thin film of the transducer 114 is vibrated in order to generate an ultrasonic pulse. The generated ultrasonic pulse is irradiated onto an object, for example, an object in a human body. The irradiated ultrasonic pulse is reflected by at least one targeted part that is positioned at any of various depths inside the object. The transducer 114 collects an echo ultrasonic wave, which is the ultrasonic pulse reflected by the targeted part and returned, and converts the collected echo ultrasonic wave into an ultrasonic echo signal, which is an electrical signal.

The converted ultrasonic echo signal may be focused by a beamformer, which will be described below, in order to enhance resolution of an ultrasonic image. The echo ultrasonic wave and the ultrasonic echo signal have different forms, i.e., a wave and an electrical signal, respectively, but contain the same information on the object and indicate a previous stage for generating an ultrasonic image. For convenience of description, hereinafter, the echo ultrasonic wave and the ultrasonic echo signal are considered to have the same meaning, since both the echo ultrasonic wave and the ultrasonic echo signal are reflected from the object and received and/or processed by the transducer.

When respective elements collect echo ultrasonic waves originating from an image point, the echo ultrasonic waves reach respective elements along different traveling paths, thus causing a difference between propagation distances. The difference between propagation distances results in a difference in times taken for the echo ultrasonic waves to reach respective elements. Thus the collected echo ultrasonic waves are required to be focused in consideration of the time taken to travel the distance.

First, the difference in times taken for the echo ultrasonic waves to reach respective elements, i.e., a delay is found. Next, when the collected echo ultrasonic waves are focused, a subsequent collected echo ultrasonic wave is phase-compensated by the delay, and thus the echo ultrasonic waves originating from the image point reaches all elements at the same time. As a result, if the collected echo ultrasonic waves are added together, the added amplitude is maximized, because all the received echo ultrasonic waves have the same phase as each other.

Figure 4:
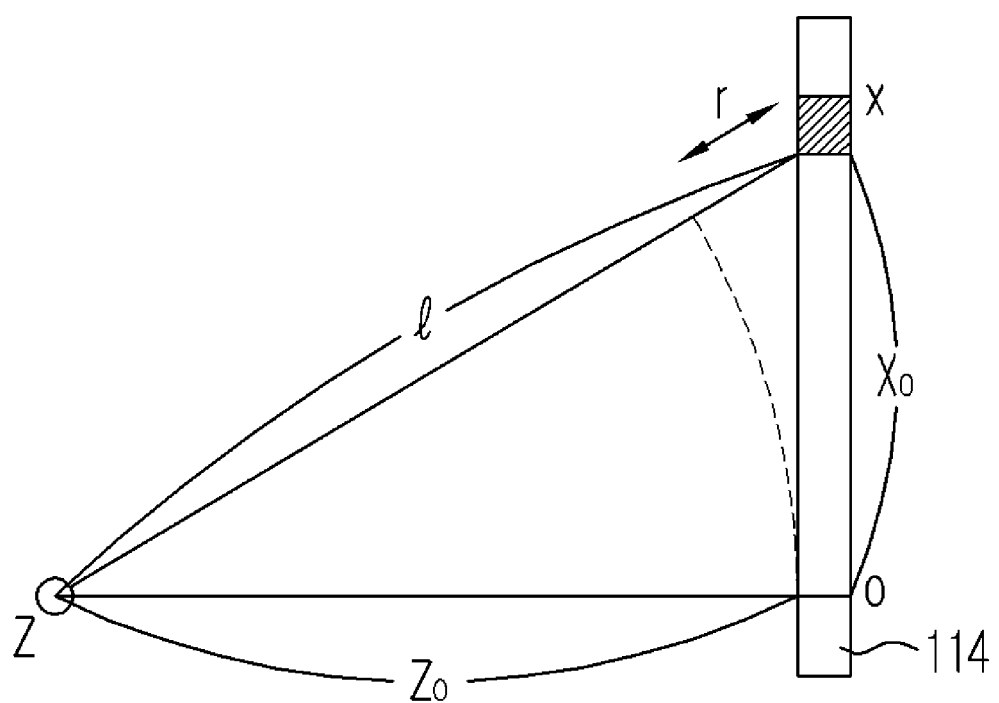
FIG. 4 is a view showing a method of focusing an echo ultrasonic wave using a transducer, according to an exemplary embodiment.

FIG. 4 is a view which illustrates a method of finding a delay occurring when an echo ultrasonic wave reaches an element. An echo ultrasonic wave that is reflected from an image point Z and returned to an element arranged in a center of the transducers 144 travels a distance $z_0$. However, an echo ultrasonic wave travels a distance l in order to reach an element arranged at a distance x from the center, thus delaying an arrival time according to a distance r. A delay of the echo ultrasonic wave reaching the element arranged at the distance x from the center with respect the element arranged at the center may be calculated by using Equation 1 below:

$$\tau = \frac{r}{c_0} = \frac{\sqrt{z_0^2 + x^2} - z_0}{c_0} \qquad \text{[Equation 1]}$$

where $c_0$ is an ultrasonic sound velocity in a corresponding medium, r is a difference between a distance that the echo ultrasonic wave travels to the element having the delay to be calculated and a distance that the echo ultrasonic wave travels to the center of the transducers 114, i.e., a focusing distance, $z_0$ is a distance from the center of the transducers 114 to a focusing point, and x is a distance from the center of the transducers 114 to the element having the delay to be calculated.

In Equation 1, $z_0$ and x are known values, and thus the sound velocity $c_0$ is required to be accurately found in order to calculate the delay $\tau$. When a focusing delay is not accurate, the phases of the echo ultrasonic waves collected by the respective elements are different, thus reducing the amplitude of the focused echo ultrasonic wave. When the echo ultrasonic waves are focused based on an inaccurate sound velocity, a delay $\tau'$ of the echo ultrasonic wave may be calculated by using Equation 2 below:

$$\tau' = \frac{r}{c_0 + \partial c} = \frac{r}{c_0}\left(\frac{c_0}{c_0 + \partial c}\right) \qquad \text{[Equation 2]}$$

where $c_0$ is an ultrasonic sound velocity in a corresponding medium, $\partial_c$ is an error in the ultrasonic sound velocity in the corresponding medium, r is a focusing distance, $z_0$ is a distance from the center of the transducers 114 to a focusing point, and x is a distance from the center of the transducers 114 to the element having the delay to be calculated.

As seen in Equation 2, the focusing delay is associated with a change rate $$\left(\frac{c_0}{c_0 + \partial c}\right)$$

of the sound velocity. Since a focusing time is changed according to a change in the focusing delay, the image point seems to move in a depth direction from its original position.

In general, the sound velocity used to calculate the delay in the ultrasonic apparatus may be approximately equal to 1540 meters per second, which is an average sound velocity in a human soft tissue. However, since velocities of the ultrasonic wave vary significantly depending on an object or medium characteristics of the object, a large error may occur when the focusing delay is calculated using a fixed velocity. The inaccurate focusing delay causes a major lobe to be widened and a minor lobe to be increased in sound field characteristics, thus reducing resolution of an ultrasonic image. In addition, wrong information may be also delivered with respect to calculating a volume ratio of a heart or kidney, which requires a geometric size or distance information of the medium. Accordingly, finding an accurate sound velocity of the ultrasonic wave in the medium is important to enhance the resolution.

In order to accurately measure the sound velocity of the ultrasonic wave in the medium, a difference between an irradiation time of the ultrasonic wave and a collection time of the echo ultrasonic wave may be used. The ultrasonic wave irradiated by the transducer 114 is reflected by the medium inside the object. An echo ultrasonic wave, which is the reflected ultrasonic wave, is collected by the transducer 114. Accordingly, the sound velocity of the ultrasonic wave in the medium may be acquired by dividing the traveling distance of the ultrasonic wave and the echo ultrasonic wave by the difference between the time of irradiation of the ultrasonic wave and the time of collection of echo ultrasonic wave.

Figure 5A:
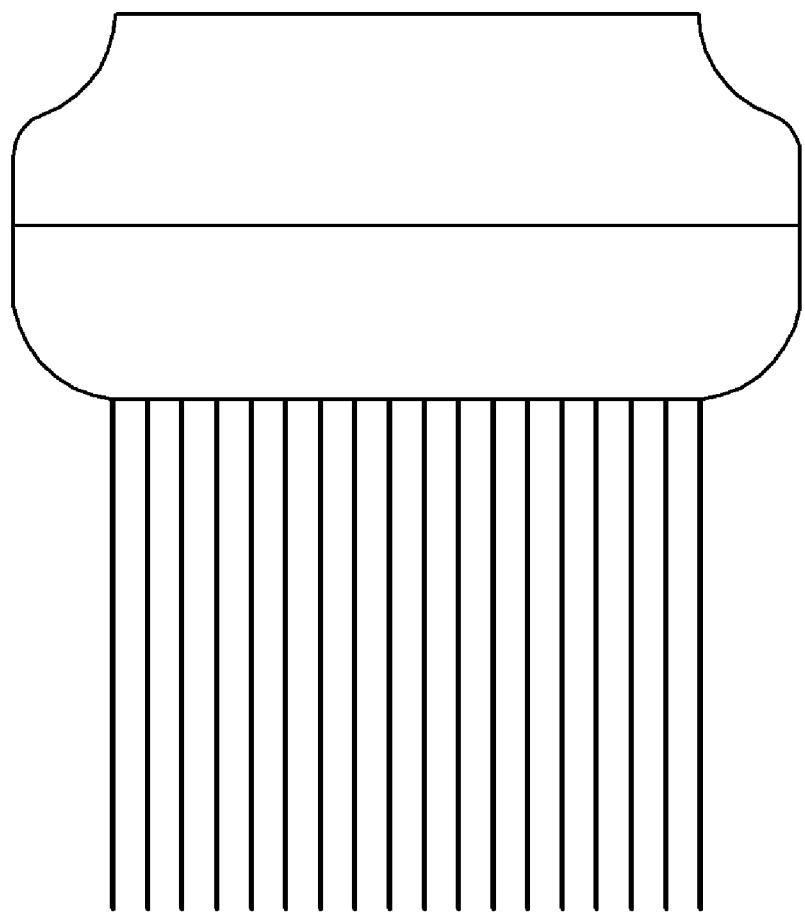
FIG. 5A is a view showing a method of a transducer irradiating an ultrasonic wave directly forward, according to an exemplary embodiment.

FIG. 5A is a view which illustrates a method of a transducer irradiating an ultrasonic wave directly forward, according to an exemplary embodiment. Since the ultrasonic wave irradiated from the transducer 114 to the object travels directly forward, a traveling distance of the ultrasonic wave may be replaced by a distance between the transducer 114 and the medium. Accordingly, the sound velocity of the ultrasonic wave in the medium may be found by dividing twice the distance between the transducer 114 and the medium by the time difference between the irradiation and collection of the ultrasonic wave.

However, in consideration of traveling characteristics of ultrasonic sound field, it is difficult to acquire accurate information which relates to a boundary surface parallel to a scanning line, compared to a boundary surface of a tissue perpendicular to the scanning line. Accordingly, this problem should be solved by allowing the irradiated ultrasonic wave to have various irradiation angles.

Figure 5B:
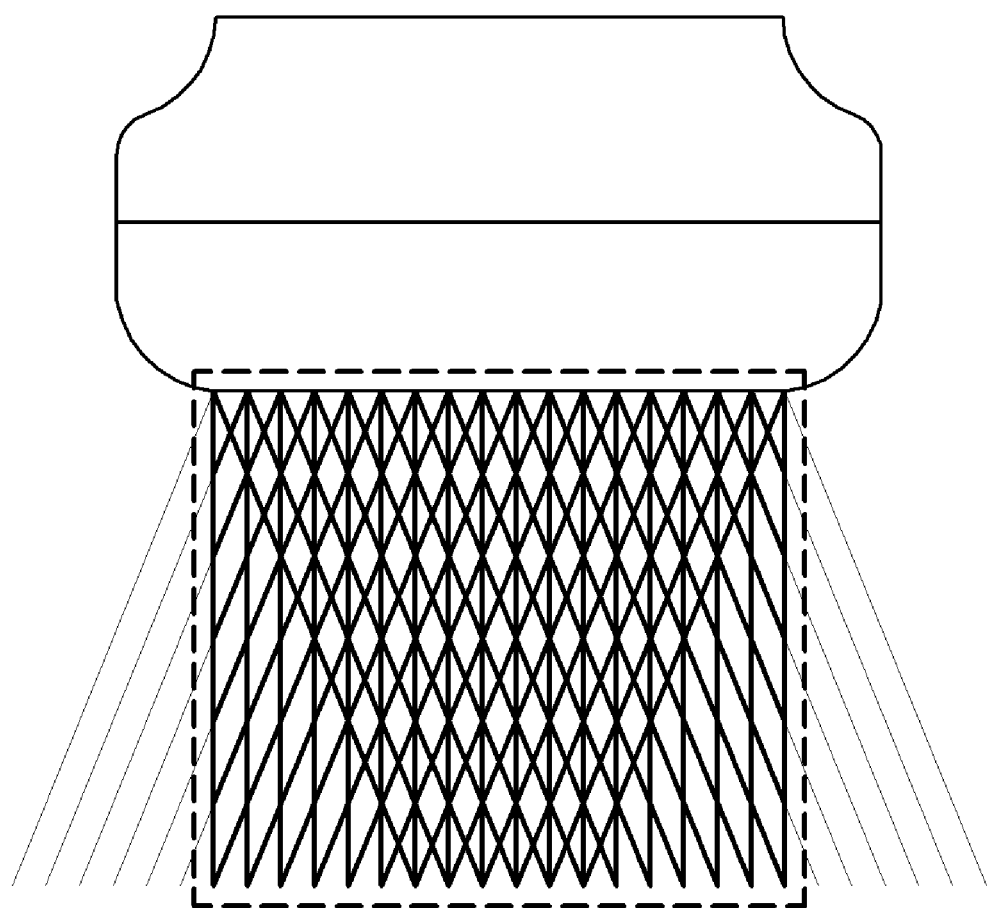
FIG. 5B is a view showing a method of a transducer irradiating an ultrasonic wave in various directions, according to an exemplary embodiment.

FIG. 5B is a view which illustrates a method of a transducer irradiating an ultrasonic wave in various directions, according to an exemplary embodiment. When an ultrasonic wave is irradiated onto an object in several directions rather than in only one direction, more information relating to the object may be acquired, as compared to the single directional irradiation. In particular, when an ultrasonic wave is irradiated toward a medium inside the object at various angles and a plurality of sound velocities are found, a more accurate sound velocity of the ultrasonic wave may be acquired by using the plurality of sound velocities.

FIG. 5B illustrates an example in which ultrasonic waves are irradiated in three directions from the transducer toward the object. The sound velocities of the ultrasonic waves from different directions are measured in the same area (inside a dashed-line square), thus increasing accuracy as compared to the measured sound velocity of the ultrasonic wave from one direction. In the area inside the dashed-line square, ultrasonic waves having different respective traveling directions overlap. In such an overlapping region, composite data may be generated via compounding. The compounding will be described below.

As described above, the ultrasonic probe 110 may have different types, depending on a form of arrangement of transducers 114. Depending on the types of the ultrasonic probe 110, an ultrasonic wave may be irradiated at various irradiation angles, which means that a plurality of ultrasonic waves are irradiated in different traveling directions.

Figure 6A:
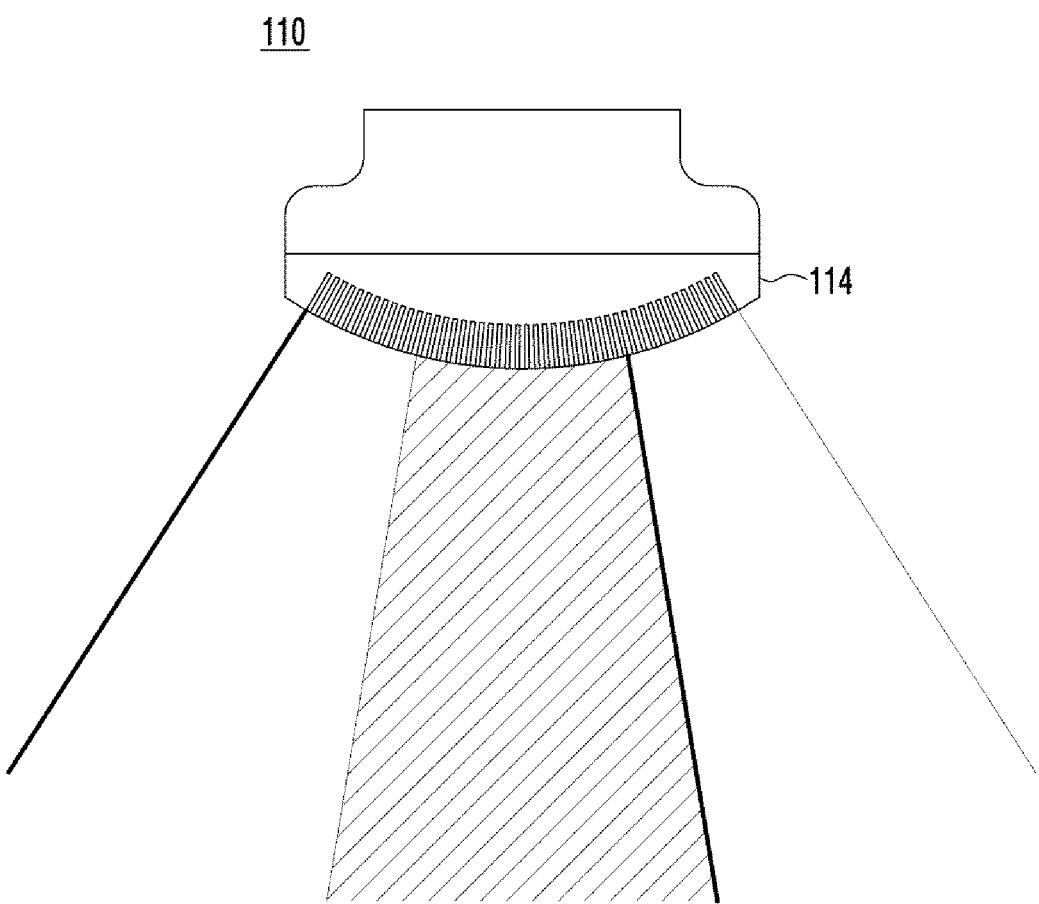
FIG. 6A is a view showing a method of a convex array probe irradiating an ultrasonic wave at various irradiation angles, according to an exemplary embodiment.
Figure 6B:
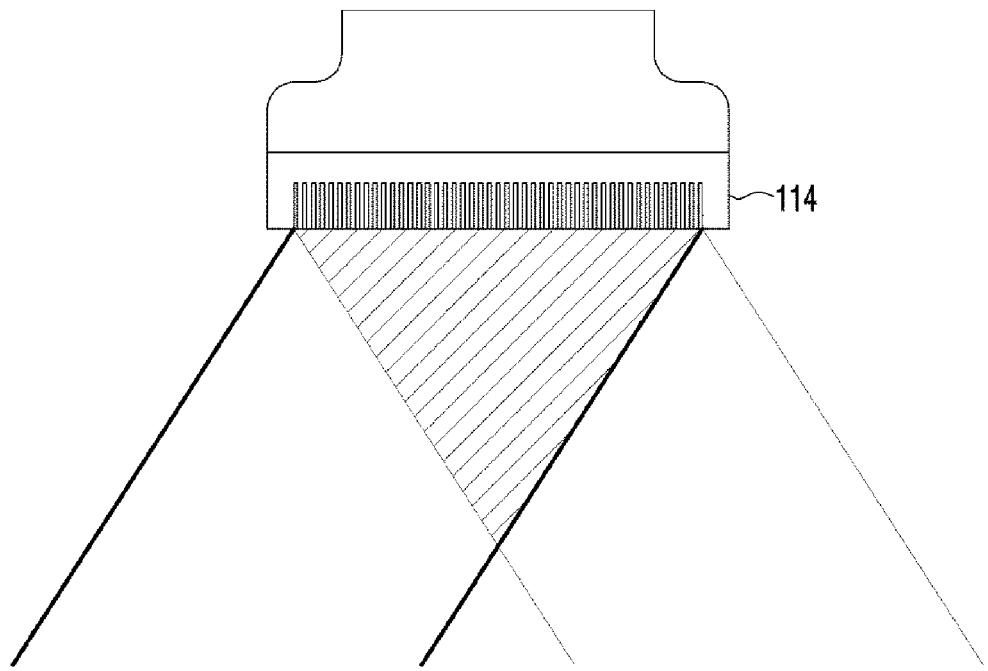
FIG. 6B is a view showing a method of a linear array probe irradiating an ultrasonic wave at various irradiation angles, according to an exemplary embodiment.

FIG. 6A is a view which illustrates a method of a convex array probe irradiating an ultrasonic wave at various irradiation angles, according to an exemplary embodiment, and FIG. 6B is a view which illustrates a method of a linear array probe irradiating an ultrasonic wave at various irradiation angles, according to an exemplary embodiment. A solid line and a dashed line indicate ultrasonic waves that are irradiated from each transducer 114 and have different traveling directions, respectively.

In a convex array probe, since the transducers 144 are arranged along a predetermined curved surface, an ultrasonic wave travels in the form shown in FIG. 6A. Accordingly, if a position of the ultrasonic probe 110 is mechanically moved, a plurality of ultrasonic waves having different traveling directions may be irradiated. Referring to FIG. 6A, ultrasonic waves may be irradiated in a solid-line direction and a dashed-line direction, and in this case, compounding may be performed on an overlapping region.

Unlike the convex array probe, the linear array probe may generate only an ultrasonic wave that travels directly forward. In this case, in order to change a traveling direction of the irradiated ultrasonic wave, the ultrasonic wave may be steered to another direction by using electronic calculation.

Each element of the linear array probe performs focusing with its own delay upon irradiating an ultrasonic wave. When the focusing is controlled such that a plurality of elements may have symmetrical delays with respect to the center of the elements, an element positioned at the center appears to irradiate the ultrasonic wave, which is called a scan line. In particular, if some elements have asymmetrical delays, the scan line is formed at a certain angle. This may have the same effect as an ultrasonic wave being bent and then irradiated in an opposite direction. In FIG. 6B, respective ultrasonic waves travel along the solid line and dashed line by steering the linear array probe, and compounding may be performed on an overlapping portion.

Alternatively, a two-dimensional (2D) array probe enables an ultrasonic wave to be steered so as to be irradiated in more various directions. Specifically, a one-dimensional (1D) array probe, such as a convex array probe or a linear array probe, allows irradiation of only an ultrasonic wave traveling in the same plane, and a 2D array probe in which elements are arranged in 2D allows irradiation of ultrasonic waves traveling in different planes, thereby enabling the traveling direction of the ultrasonic wave to be expressed as a 3D vector. A spatial composite sound velocity may be acquired from an object by using such a characteristic, which will be described below.

As such, when a plurality of ultrasonic waves having different traveling directions are irradiated onto an object, a plurality of echo ultrasonic waves corresponding thereto may be acquired. In this case, an irradiation time of the ultrasonic wave and a collection time of the echo ultrasonic wave may be delivered to the main body 100 through a wired or wireless communication network.

Referring back to FIG. 3, a controller 200 may be configured to acquire sound velocities of ultrasonic waves having different traveling directions and compound the acquired sound velocities in order to determine a composite sound velocity. In this case, the sound velocity may be acquired using the irradiation time of the ultrasonic wave and the collection time of the echo ultrasonic wave which are delivered from the transducers 114. The method is merely an example of a method for acquiring the sound velocity according to an exemplary embodiment. However, the present inventive concept is not limited to the above example.

Specifically, the controller 200 may include a sound velocity acquisition unit (also referred to herein as a "sound velocity acquisition component" and/or as a "sound velocity acquirer") 210 configured to acquire sound velocities of ultrasonic waves having different traveling directions from the difference between the irradiation time of the ultrasonic wave and the collection time of the echo ultrasonic wave, and a calculation unit (also referred to herein as a "calculator") 220 configured to compound the acquired sound velocities in order to determine a composite sound velocity. Furthermore, the controller 200 may include a planar composition unit (also referred to herein as a "planar composition component" and/or as a "planar composer") 230 configured to compound planar composite sound velocities in order to determine a spatial composite sound velocity when the acquired composite sound velocity is a planar composite sound velocity. Each of the sound velocity acquisition unit 210, the calculation unit 220, and the planar composition unit 230 may be implemented as a hardware component, such as a special-purpose processor and/or as circuitry, or as a software module.

The sound velocity acquisition unit 210 may use the delivered difference between the irradiation time of the ultrasonic wave and the collection time of the echo ultrasonic wave in order to acquire a sound velocity in a medium inside the object. As described above, the sound velocity of the ultrasonic wave in the medium may be acquired by dividing the traveling distance of the ultrasonic wave and the echo ultrasonic wave by the difference between the irradiation time of the ultrasonic wave and the collection time of the echo ultrasonic wave. In this case, if the traveling direction of the ultrasonic wave is not perpendicular to the surface of the medium, a trigonometric function may be used to find the traveling distance of the ultrasonic wave and the echo ultrasonic wave according to a method of acquiring the sound velocity according to an exemplary embodiment.

Figure 7:
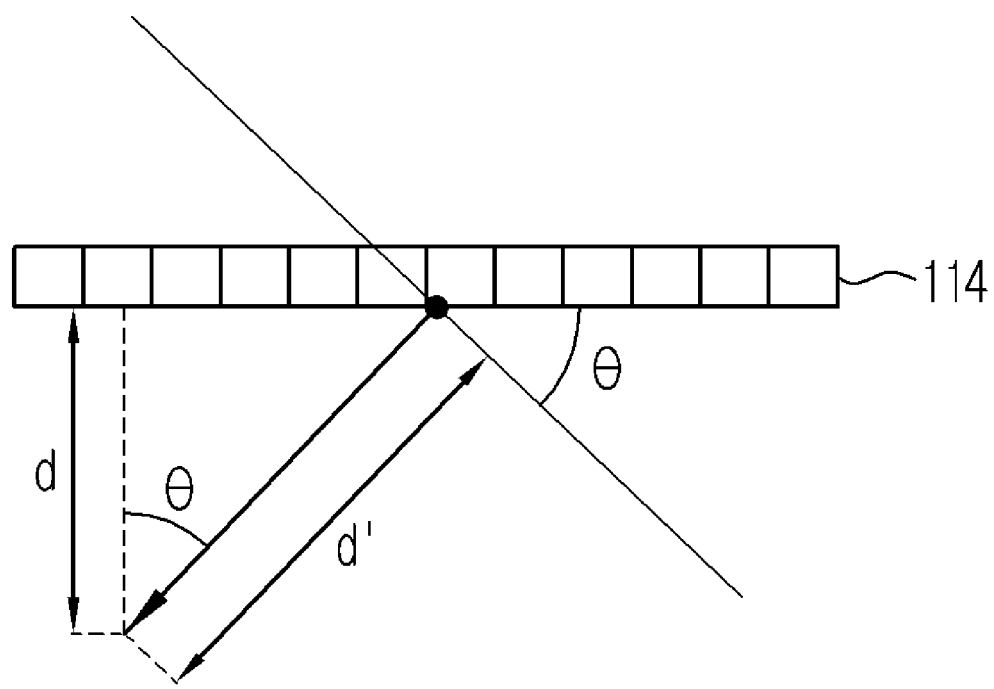
FIG. 7 is a view showing a method of finding a traveling distance when an ultrasonic wave is steered while being irradiated, according to an exemplary embodiment.

FIG. 7 is a view which illustrates a method of finding a traveling distance when an ultrasonic wave is steered while being irradiated, according to an exemplary embodiment. In FIG. 7, $\theta$ is a steering angle and d is a distance between the transducer 114 and the medium inside the object, and d' is a distance from an element irradiating an ultrasonic wave onto an object, i.e., a traveling distance of the ultrasonic wave.

On the assumption that a distance d between the transducer 114 and the medium inside the object is known, the steering angle $\theta$ may be used in order to find the traveling distance d' of the ultrasonic wave. The traveling distance d' of the ultrasonic wave may be calculated by using Equation 3 below:

$$d' = \frac{d}{\cos\theta}. \quad \text{[Equation 3]}$$

The sound velocity of the ultrasonic wave in the medium may be acquired by dividing twice the traveling distance of the ultrasonic wave obtained through such a process by the difference between the irradiation time of the ultrasonic wave and the collection time of the echo ultrasonic wave. A plurality of sound velocities may be acquired by irradiating an ultrasonic wave several times while varying a steering angle with respect to the same medium.

The calculation unit 220 may compound the plurality of sound velocities acquired according to the traveling direction of the ultrasonic wave in order to determine a composite sound velocity. In this case, the compounding may be performed based on a compounding algorithm that is previously stored or inputted by a user, or based on an internal calculation.

The compounding process includes the use of an ultrasonic wave technique for combining several screens acquired at different angles in order to acquire one complex image. With this technique, it is possible to reduce an artifact of an image to increase an image quality, as compared to an existing ultrasonic technique. It is also possible to quantitatively reduce a speckle noise in the complex image, thus facilitating discovery of a lesion, especially when the contrast is low, and determination of a boundary of the lesion. Accordingly, the enhanced complex image may be acquired by suppressing artifacts such as a speckle noise.

Figure 8A:
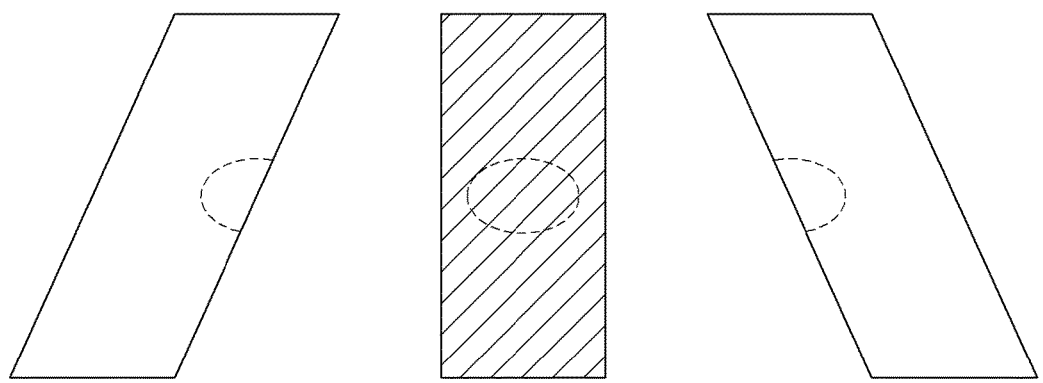
FIGS. 8A and 8B are views showing a process of acquiring a complex image via compounding, according to an exemplary embodiment.
Figure 8B:
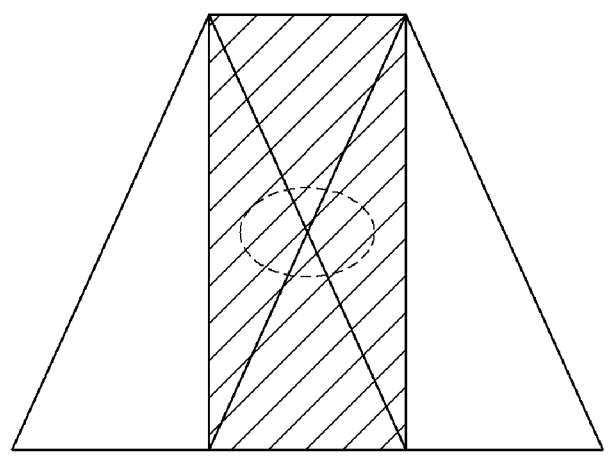

FIGS. 8A and 8B are views which illustrate a process of acquiring a complex image via compounding according to an exemplary embodiment. As shown in FIG. 8A, ultrasonic waves having different directions are irradiated onto an object, and thus a plurality of ultrasonic images are acquired. The left image is acquired by irradiating an ultrasonic wave at a 45 degree angle to the left, the middle image is acquired by irradiating an ultrasonic wave directly forward, and the right image is acquired by irradiating an ultrasonic wave at a 45 degree angle to the right. A dashed-circle part denotes an object in each ultrasonic image. It can be seen that a figure of an object shown in an ultrasonic image varies with respect to a traveling direction of the ultrasonic wave. FIG. 8A illustrates an example in which that ultrasonic waves are irradiated in three directions. However, the number of the irradiation directions is not limited thereto, and may be two or more.

FIG. 8B shows a process of compounding a plurality of ultrasonic images acquired as shown in FIG. 8A in order to acquire a composite image. When respective images are adjusted to overlap in consideration of steering angles, an overlapping region corresponds to the composite image. A dark region in FIG. 8B is an image overlapping region in FIG. 8A, which indicates the composite image. A pixel value in the overlapping region may be determined by a compounding algorithm.

The compounding technique is applicable to an ultrasonic parametric image acquired by imaging detailed characteristics of an object in addition to a general ultrasonic image. Recently, research has been conducted on a technique for applying the compounding technique to ultrasonic elastography.

The compounding technique may be applied to a sound velocity, which is a critical parameter in an ultrasonic diagnosis. The calculation unit 220 may be configured to receive the plurality of sound velocities acquired for each of several respective directions from the sound velocity acquisition unit 210 and to compound the plurality of sound velocities in order to determine the composite sound velocity.

The calculation unit 220 may perform the compounding according to a compounding algorithm in order to determine the composite sound velocity. The result may vary according to the compounding algorithm, and the compounding algorithm may be selected by an input provided by a user or an internal calculation. A mean algorithm, a median filtering algorithm, a root mean square algorithm, a maximum algorithm, and a minimum algorithm will be described below as respective exemplary embodiments of the compounding algorithm.

The mean algorithm (or the linear average algorithm) is a composite algorithm, which is the most common and widely used in current medical devices. For example, one type of mean algorithm may be expressed as "All N number of values of A are added and then divided by N." The mean algorithm may be calculated by using Equation 4 below:

$$comp_{mean} = \frac{A_1 + A_2 + A_3 + \ldots + A_N}{N} \quad \text{[Equation 4]}$$

where $comp_{mean}$ is a composite sound velocity at a specific position of an object, A is an ultrasonic sound velocity based on a traveling direction, and N is the number of traveling directions of the ultrasonic wave.

The median filtering algorithm is a filtering technique for smoothing all values with reference to ambient values. When values in a specific region are aligned in order of size, a median is an output value. A one-dimensional (1D) median filter is applied to the plurality of sound velocities. The median filtering algorithm may be calculated by using Equation 5 below:

$$comp_{median} = \text{median}(A_1, A_2, A_3, \ldots, A_N) \quad \text{[Equation 5]}$$

where $comp_{median}$ is a composite sound velocity at a specific position of an object, A is an ultrasonic sound velocity based on a traveling direction, and N is the number of traveling directions of the ultrasonic wave.

The root mean square algorithm may assign a weight to the magnitude of the sound velocity by using the square of the sound velocity. The root mean square algorithm may be calculated by using Equation 6 below:

$$comp_{rms} = \frac{\sqrt{(A_1^2 + A_2^2 + A_3^2 + \ldots + A_N^2)}}{N} \quad \text{[Equation 6]}$$

where $comp_{rms}$ is a composite sound velocity at a specific position of an object, A is an ultrasonic sound velocity based on traveling direction, and N is the number of traveling directions of the ultrasonic wave.

The maximum algorithm compares sound velocities and determines the maximum sound velocity as the composite sound velocity. The maximum algorithm may be calculated by using Equation 7 below:

$$comp_{max} = \max(A_1, A_2, A_3, \ldots, A_N) \quad \text{[Equation 7]}$$

where $comp_{max}$ is a composite sound velocity at a specific position of an object, A is an ultrasonic sound velocity based on a traveling direction, and N is the number of traveling directions of the irradiated ultrasonic wave.

The minimum algorithm compares sound velocities with each other and determines the minimum sound velocity as the composite sound velocity. The minimum algorithm may be calculated by using Equation 8 below:

$$comp_{min} = \min(A_1, A_2, A_3, \ldots, A_N) \quad \text{[Equation 8]}$$

where $comp_{min}$ is a composite sound velocity at a specific position of an object, A is an ultrasonic sound velocity based on a traveling direction, and N is the number of traveling directions of the irradiated ultrasonic wave.

Another compounding algorithm may be used in addition to the above-described compounding algorithms. The ultrasonic apparatus and the control method for the same according to an exemplary embodiment are not limited thereto.

The calculation unit 220 may be configured to compound a plurality of sound velocities in order to determine a composite sound velocity. In this case, the composite sound velocity may be a planar composite sound velocity. When the transducers 114 are arranged in one dimension (for example, in a z-axis direction), an ultrasonic wave irradiated by each of the transducers 114 travels in the same plane (for example, x-z plane). In addition, since steering is performed along a direction (z axis) in which the transducers 114 are arranged, ultrasonic waves irradiated before and after the steering travel in the same plane (for example, x-z plane), although directions in which the ultrasonic waves travel are different. Accordingly, information which relates to a cross section of an object in the plane (for example, x-z plane) in which the ultrasonic waves travel may be obtained. In this case, the information may include sound velocities. Hereinafter, each of the acquired sound velocities is referred to as a planar composite sound velocity.

Figure 9A:
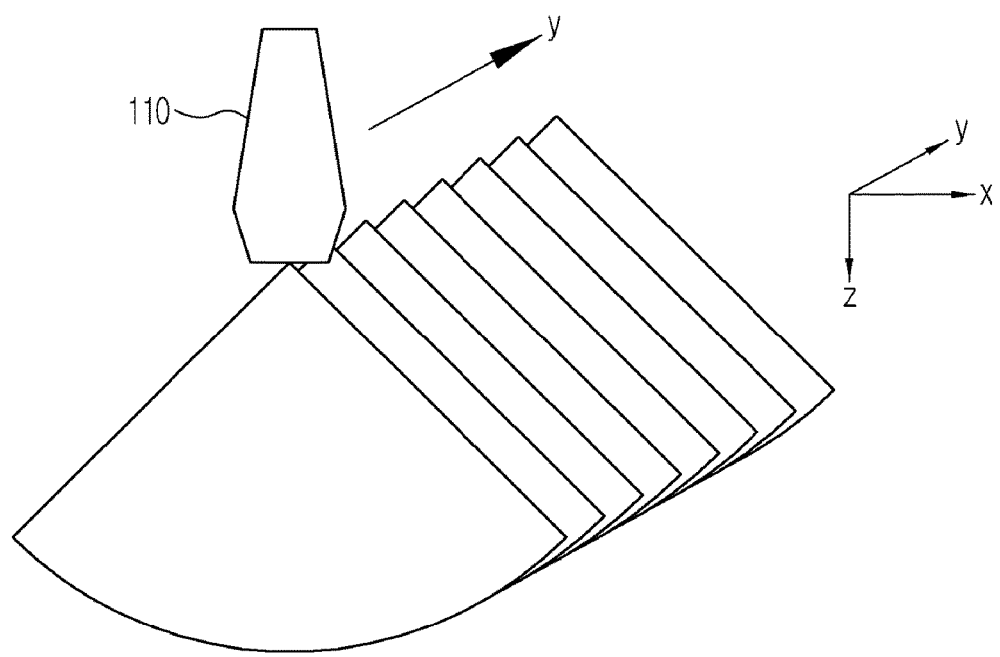
FIG. 9A is a view showing a method of irradiating an ultrasonic wave to acquire volume data of an object, according to an exemplary embodiment.

The planar composition unit 230 may be configured to compound the acquired planar composite sound velocities in order to determine a spatial composite sound velocity. FIG. 9A is a view which illustrates a method of irradiating an ultrasonic wave to acquire volume data of an object, according to an exemplary embodiment. As shown in FIG. 9A, in general, the volume data of the object is acquired by acquiring and combining information which relates to a plurality of cross sections. While the ultrasonic probe 110 is moved in a direction (y-axis) perpendicular to the cross sections, information which relates to each of the cross sections is acquired and added in order to acquire volume data.

When desired volume data is an ultrasonic sound velocity in an object, the volume data may be acquired by irradiating a plurality of ultrasonic waves that travel in different directions in different planes toward the object and classifying sound velocities of the plurality of ultrasonic waves that travel in each plane. If the classified sound velocities are compounded, a planar composite sound velocity in the object corresponding to each plane may be determined. Furthermore, a spatial composite sound velocity in the object may be determined by compounding the planar composite sound velocities determined for the respective planes.

Figure 9B:
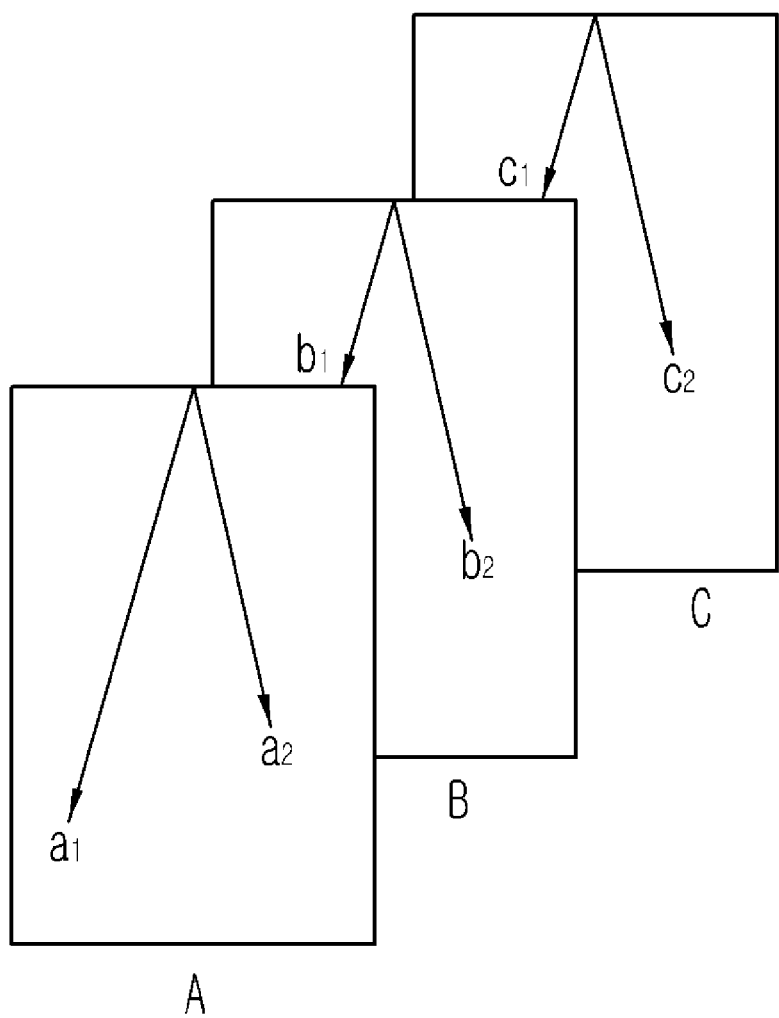
FIG. 9B is a view showing a method of irradiating a plurality of ultrasonic waves onto a plurality of planes to acquire a spatial composite sound velocity, according to an exemplary embodiment.

Specifically, referring to FIG. 9B, a plurality of respective ultrasonic waves $a_1$, $a_2$, $b_1$, $b_2$, $c_1$, and $c_2$ which travel in different directions in a plurality of corresponding planes A, B, and C may be irradiated onto an object. In this case, it is assumed that $a_1$ and $a_2$, which travel in the plane A, are included in an ultrasonic group A, $b_1$ and $b_2$, which travel in the plane B, are included in an ultrasonic group B, and $c_1$ and $c_2$, which travel in the plane C, are included in an ultrasonic group C.

A sound velocity of an ultrasonic wave is acquired for each group. In particular, a sound velocity of the ultrasonic group A ($a_1$ and $a_2$), which travels in the plane A, is acquired, a sound velocity of the ultrasonic group B ($b_1$ and $b_2$), which travels in the plane B, is acquired, and a sound velocity of the ultrasonic group C ($c_1$ and $c_2$), which travels in the plane C, is acquired.

Sound velocities are classified and acquired for each group, and then the plurality of sound velocities in the same group are compounded. Accordingly, sound velocities of the ultrasonic waves $a_1$ and $a_2$ in the ultrasonic group A are compounded. A result (a) of the compounding of the sound velocities of the ultrasonic waves $a_1$ and $a_2$ indicates a planar composite sound velocity in an object corresponding to the plane A. Similarly, a planar composite sound velocity (b) in the object corresponding to the plane B may be determined by compounding the sound velocities of the ultrasonic waves $b_1$ and $b_2$, and a planar composite sound velocity (c) in the object corresponding to the plane C may be determined by compounding sound velocities of the ultrasonic waves $c_1$ and $c_2$.

A spatial composite sound velocity may be determined based on the planar composite sound velocities determined via the above-described process. In FIG. 9B, a spatial composite sound velocity in an object may be determined by compounding planar composite sound velocities a, b, and c in an object corresponding to the planes A, B, and C.

Unlike in FIGS. 9A and 9B, which show that a planar composite sound velocity may be determined while moving the ultrasonic probe 110 in a direction (y-axis) perpendicular to the cross sections, the cross sections used to acquire the planar composite sound velocity may intersect with one another. In this case, an intersection region may be in the form of a straight line, and the planar composition unit 230 may perform the compounding on the intersection region according to the above-described compounding algorithms. A spatial composite sound velocity may also be determined via such a method.

Figure 10:
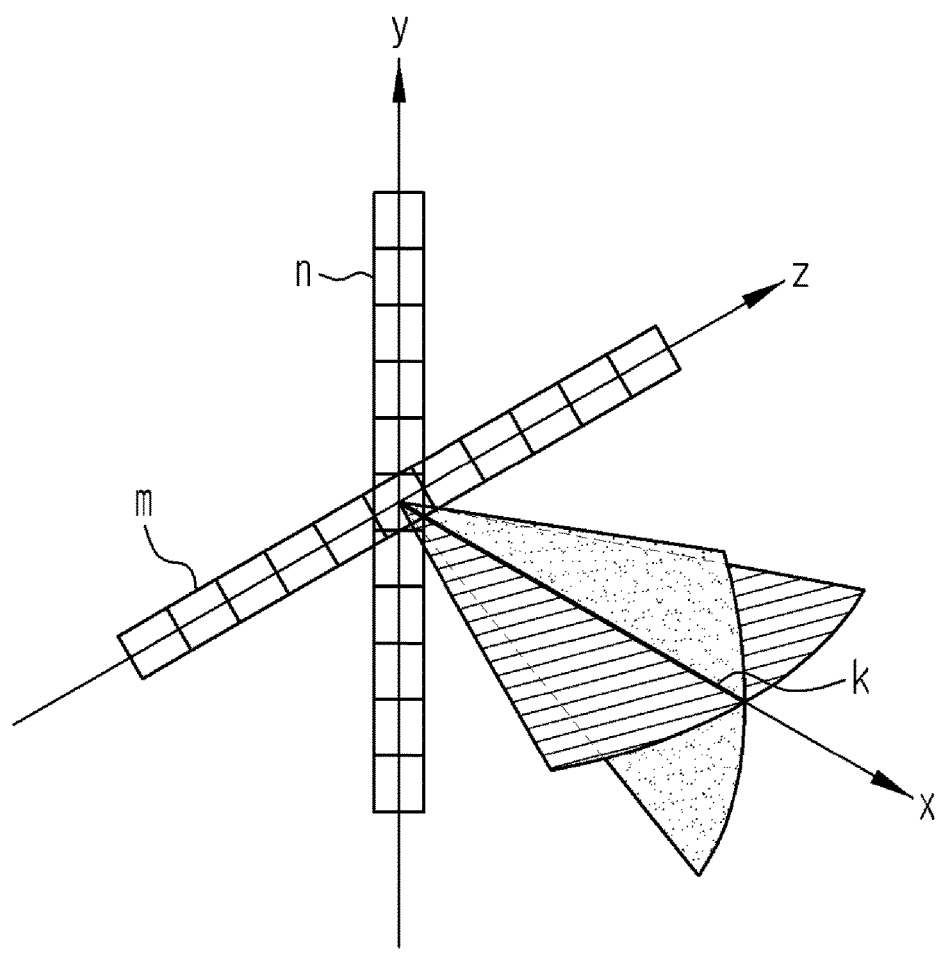
FIG. 10 is a view showing an example in which a vertical cross section of an object is used to acquire a planar composite sound velocity, according to an exemplary embodiment.

FIG. 10 is a view which illustrates an example in which a vertical cross section of an object is used to acquire a planar composite sound velocity according to an exemplary embodiment. First, an element arrangement direction of the transducers 114 may be adjusted to a z-axis and then an ultrasonic wave may be irradiated (m). A planar composite sound velocity in a cross section of an object in an x-z plane may be acquired based on the irradiated ultrasonic wave. Subsequently, the element arrangement direction of the transducers 114 may be adjusted to a y-axis and then an ultrasonic wave may be irradiated (n). As a result, a planar composite sound velocity in a cross section of an object in an x-y plane may be acquired. In this case, an intersection region k is formed along an x-axis, and a sound velocity therein may be determined by compounding the planar composite sound velocities for the cross sections.

FIG. 10 shows that a planar composite sound velocity in a vertical cross section of an object is acquired when the transducers are arranged in one dimension. However, the transducers may be arranged in two dimensions. In this case, a spatial composite sound velocity may be acquired by electrically irradiating a plurality of ultrasonic waves traveling in different planes to an object while an ultrasonic probe is not physically moved.

Since the planar composite sound velocity is acquired by irradiating ultrasonic waves traveling in the same plane, the planar composite sound velocity may be expressed as a two-dimensional (2D) vector. However, the object is actually in the three-dimensional (3D) form, and thus the sound velocity should be expressed as a 3D vector in order to have a more accurate value. As such, the sound velocity expressed as the 3D vector may be determined by compounding planar composite sound velocities into a spatial composite sound velocity. The determined sound velocity may be closer to an actual sound velocity, as compared to the sound velocity that is expressed as a 2D vector.

The composite sound velocity which is determined via such a process is a critical parameter when a beam is formed. Referring to FIG. 3, a beamformer 170 may be configured to delay an echo ultrasonic wave based on a composite sound velocity, to focus the delayed echo ultrasonic wave, and to convert the focused echo ultrasonic wave into an ultrasonic image signal. The display 160 may receive the ultrasonic image signal from the beamformer 170 and display the received ultrasonic image signal on a screen.

As described above, the collected echo ultrasonic waves have the same phase as a result of a process which includes measuring a difference in time taken for each echo ultrasonic wave to reach an element, delaying the echo ultrasonic waves based on the time difference, and focusing the delayed echo ultrasonic waves, thus maximizing a sum of amplitudes of the echo ultrasonic waves. The maximized magnitude, in turn, means that a high-resolution screen can be obtained by converting the collected echo ultrasonic wave into the ultrasonic image signal. In this case, the sound velocity of the ultrasonic wave is used to calculate a delay for the echo ultrasonic wave when the focusing is performed. Accordingly, by acquiring a plurality of sound velocities acquired from several directions which are compounded in order to determine a composite sound velocity, instead of acquiring a sound velocity in only one direction, and calculating a delay due to a difference in the traveling distance, it is possible to cause the echo ultrasonic waves to have the exactly same phase, thus acquiring a high-resolution ultrasonic image. The composite sound velocity may be used to generate an ultrasonic thermal image using a relationship between a sound velocity and a temperature of an object, as well as to increase a resolution of an ultrasonic image as described above.

The ultrasonic thermal image is important to ultrasonic hyperthermia. In the ultrasonic hyperthermia process, a high intensity focused ultrasonic (HIFU) wave is used, which is a method for treating a tumor by focusing sound energy onto a small focal point by using an ultrasonic wave to generate heat of about 60 to 100 or more degrees Celsius. The HIFU treatment is harmless to humans, and has recently been in the spotlight as an environmentally-friendly treatment. For example, when solar rays are focused by a magnifying glass onto a focal point, a fire is started at the focal point, but there is no effect of the fire around the focal point. A principle of the HIFU treatment is similar to the above description.

In order to apply such an ultrasonic hyperthermia, a temperature characteristic of an object or a medium inside the object must be known. This is because it is required to be checked as to whether a region to be treated can be well burned by the HIFU, and then it is determined whether the ultrasonic hyperthermia is applied or not. Accordingly, checking and imaging of a change in temperature of an object using an ultrasonic wave is essential in removing a lesion via the ultrasonic hyperthermia process.

Scattering may occur in the object depending on a thermal expansion change and a sound velocity of an irradiated ultrasonic wave, thus enabling a temperature of the object to be estimated. A relationship between a sound velocity of an ultrasonic wave and a temperature of an object is known in the art, so a detailed description thereof will be omitted.

Referring back to FIG. 3, on the basis of the above relationship, a thermal image generator 180 may be configured to convert a composite sound velocity into a thermal image. The thermal image generator 180 generates the thermal image by setting a pixel value of the thermal image for each point of an object on the basis of a temperature which corresponds to a respective sound velocity at the point of the object.

Figure 11:
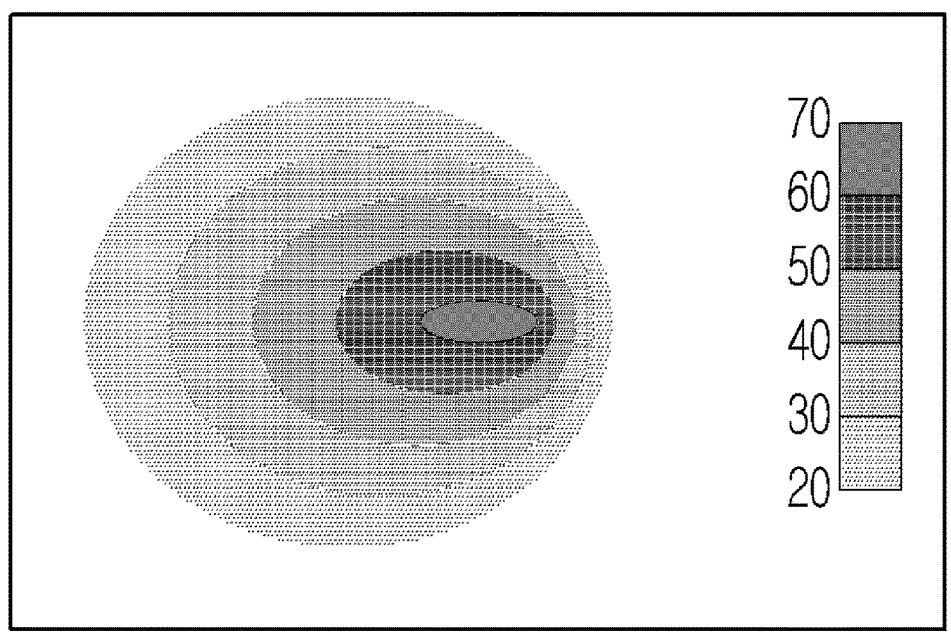
FIG. 11 is a view showing a screen for displaying a thermal image using different colors to represent different temperatures, according to an exemplary embodiment.

The display 160 may display the generated temperature on a screen. FIG. 11 is a view showing a screen for displaying a thermal image using different colors to represent different temperatures, according to an exemplary embodiment. On a right side of the screen, a color index which indicates a color corresponding to a temperature may also be displayed. When the thermal image is seen with reference to the color index, it can be seen that a central portion has a temperature of about 70 degrees, and a temperature decreases in conjunction with increasing distance from the central portion.

Unlike in FIG. 11, a temperature may be displayed as a number or character in addition to a shade or pattern. The above-described method is merely an exemplary embodiment for identifying temperatures in a thermal image. Thus, any other method of allowing a user to identify temperatures through a screen may be applied to the ultrasonic apparatus and the control method for the same, according to an exemplary embodiment.

Figure 12:
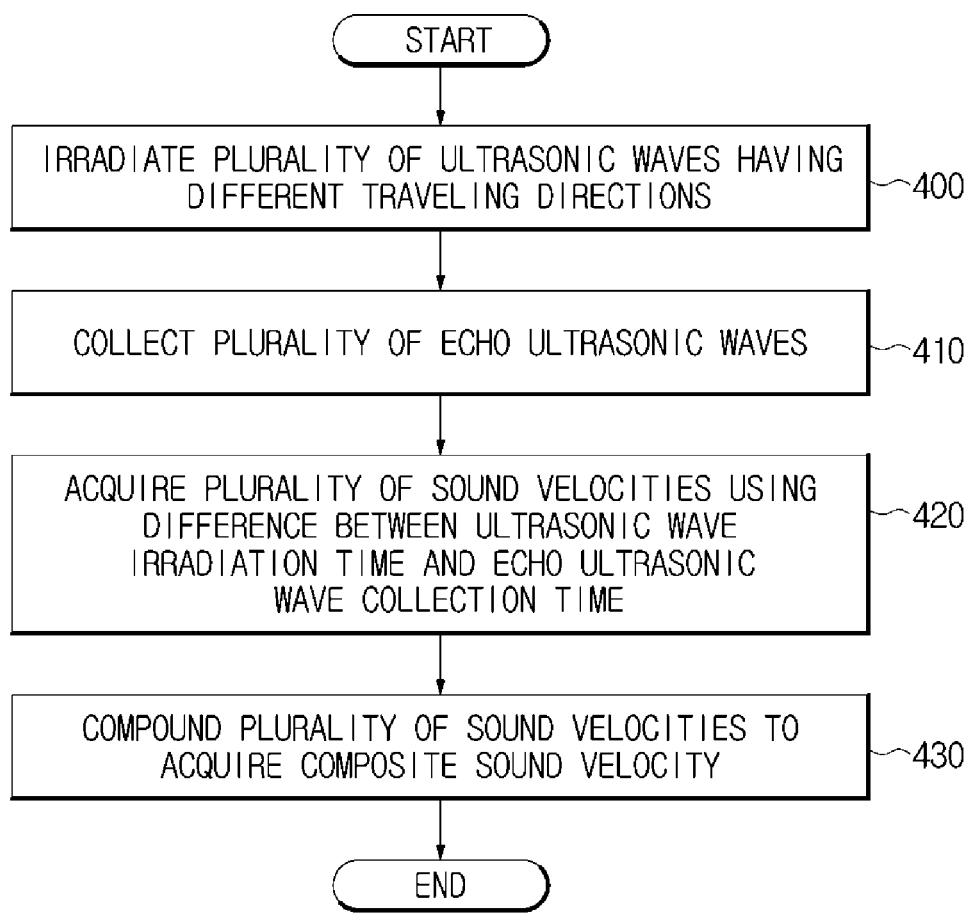
FIG. 12 is a flowchart showing a process of acquiring a composite sound velocity, according to an exemplary embodiment.

FIG. 12 is a flowchart showing a process for acquiring a composite sound velocity, according to an exemplary embodiment.

First, in operation 400, a plurality of ultrasonic waves having different traveling directions are irradiated onto an object. A method of irradiating the ultrasonic waves having different traveling directions may vary depending on the ultrasonic probe 110. For the convex array probe, a steering angle may be adjusted by a mechanical steering method, and an electronic steering method may be used in conjunction with the linear array probe, in order to irradiate ultrasonic waves having different traveling directions.

The reason for irradiating the ultrasonic waves having different traveling directions is that a method of acquiring sound velocities of the ultrasonic waves having several directions in order to determine a composite sound velocity increases accuracy, as compared to a method of measuring a sound velocity of an ultrasonic wave having only one direction.

When a plurality of ultrasonic waves are irradiated, in operation 410, a plurality of echo ultrasonic waves corresponding thereto may be collected. In this case, since the irradiated ultrasonic wave and the echo ultrasonic wave corresponding thereto may travel along the same path, the sound velocity of the ultrasonic wave may be simply found.

In particular, when a difference between an irradiation time of the ultrasonic wave and a collection time of the echo ultrasonic wave is found, in operation 420, the sound velocity may be acquired based on the difference. Since an ultrasonic wave and an echo ultrasonic wave travel along the same route, a value obtained by doubling a traveling distance is equal to a total traveling distance, and a sound velocity may be found by dividing the total traveling distance by the difference between the irradiation time of the ultrasonic wave and the collection time of the echo ultrasonic wave.

Since the sound velocity is measured from an ultrasonic wave traveling in one direction, a plurality of sound velocities corresponding to respective irradiation directions of the irradiated ultrasonic waves may be acquired.

Lastly, in operation 430, a composite sound velocity may be determined by compounding the plurality of sound velocities. Determining the composite sound velocity by compounding different sound velocities at the same point may reduce a difference with respect to an actual sound velocity.

The compounding may be performed based on a compounding algorithm that is previously stored or inputted by a user, or based on an internal calculation. The compounding algorithm includes any one or more of a mean algorithm, a median filtering algorithm, a root mean square algorithm, a maximum algorithm, and a minimum algorithm. However, each of these algorithms is merely an exemplary embodiment of the compounding algorithm, and any other algorithm for finding a composite sound velocity through the compounding may be applied.

Figure 13:
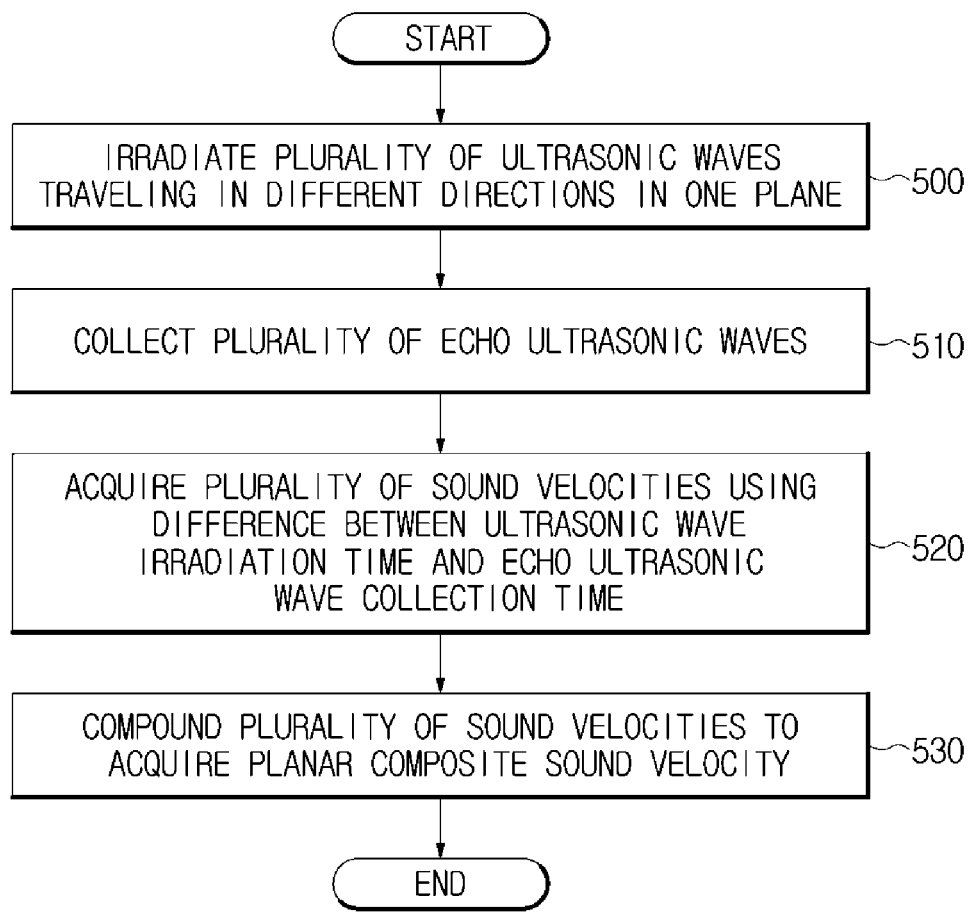
FIG. 13 is a flowchart showing a process of acquiring a planar composite sound velocity, according to an exemplary embodiment.

FIG. 13 is a flowchart showing a process for acquiring a planar composite sound velocity, according to an exemplary embodiment of the present invention. The planar composite sound velocity may be acquired on the assumption that elements of the ultrasonic probe 110 are arranged in one dimension and steering of the irradiated ultrasonic wave is performed in a direction in which the elements are arranged.

First, in operation 500, a plurality of ultrasonic waves that travels in different directions on the same plane is irradiated onto an object. If steering of the irradiated ultrasonic waves is in a direction in which the transducers 114 are arranged, the irradiated ultrasonic waves do not have a value with respect to a component perpendicular to the direction in which the elements are arranged, thus traveling in the same plane.

In operation 510, a plurality of echo ultrasonic waves may be collected corresponding to the plurality of irradiated ultrasonic waves. Thus, in operation 520, respective sound velocities of the ultrasonic waves may be acquired using a difference between an irradiation time of the ultrasonic waves and a collection time of the echo ultrasonic waves. The sound velocities of the ultrasonic waves are acquired based on the traveling directions.

Lastly, in operation 530, a planar composite sound velocity may be determined by compounding the acquired plurality of sound velocities. In this case, the acquired planar composite sound velocity refers to a sound velocity in an object corresponding to the plane where the plurality of ultrasonic waves travel.

Figure 14:
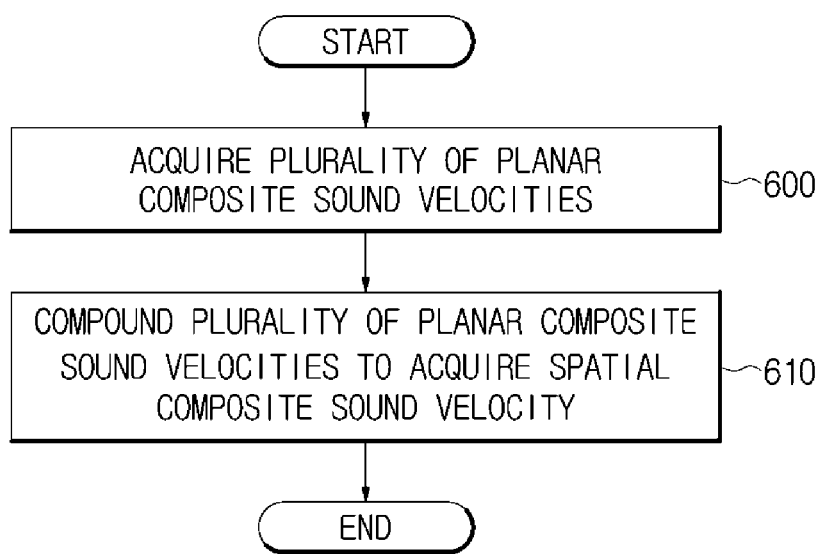
FIG. 14 is a flowchart showing a process of acquiring a spatial composite sound velocity, according to an exemplary embodiment.

FIG. 14 is a flowchart showing a process for acquiring a spatial composite sound velocity, according to an exemplary embodiment. A spatial composite sound velocity may be acquired based on the planar composite sound velocities acquired through the process shown in FIG. 13. There are several methods of acquiring the spatial composite sound velocity. However, a method of acquiring planar composite sound velocities in an object corresponding to planes intersecting with each other will be describe below. To this end, it is assumed below that planar composite sound velocities in an object corresponding to an x-z plane and an x-y plane are acquired.

First, in operation 600, planar composite sound velocities in an object corresponding to a respective plurality of planes are acquired. As assumed above, the plurality of planes may intersect with each other. Accordingly, the planar composite sound velocities in an object corresponding to an x-z plane and an x-y plane, respectively, may be acquired.

On the basis of the acquired two sound velocities, in operation 610, a spatial composite sound velocity may be determined by compounding the planar composite sound velocities in a region inside the object where the plurality of planes intersect with each other. In this aspect, the spatial composite sound velocity may be determined by compounding the acquired planar composite sound velocities with respect to an intersection region on an x-axis, which is a region where the x-y plane and the x-z plane intersect with each other. The spatial composite sound velocity determined via the compounding may be expressed in three dimensions, thereby deriving a more accurate result as compared to the planar composite sound velocity.

The ultrasonic apparatus and the control method for the same according to exemplary embodiments have the following effects.

According to an exemplary embodiment, when focusing ultrasonic waves during beamforming, the focused echo ultrasonic waves may be caused to have the same phase by setting delays based on accurate sound velocities, thus improving an image quality of an ultrasonic image.

According to another exemplary embodiment, more accurate information may be delivered to a user by displaying a thermal image of an object on a screen based on the accurate sound velocities during ultrasonic hyperthermia, thus enabling safe and effective ultrasonic treatment.

Although a few exemplary embodiments have been shown and described, it will be appreciated by those skilled in the art that changes may be made in these exemplary embodiments without departing from the principles and spirit of the present inventive concept, the scope of which is defined in the claims and their equivalents.

What is claimed is:

1. An ultrasonic apparatus comprising:
a transducer configured to irradiate a first plurality of ultrasonic waves which have different respective traveling directions onto an object and to collect a first plurality of echo ultrasonic waves reflected from the object; and
a controller configured to acquire a first plurality of respective sound velocities of the first plurality of ultrasonic waves in the object and to compound the acquired first plurality of sound velocities in order to determine a composite sound velocity in the object,
wherein a first ultrasonic wave from among the first plurality of ultrasonic waves originates from a first point and has a first traveling direction, and at least a second ultrasonic wave from among the first plurality of ultrasonic waves originates from the first point and has a second traveling direction that is different from the first traveling direction, and
wherein the controller is further configured to perform the compounding by acquiring one of a mean value, a median value, a root mean square value, a maximum value, and a minimum value of the first plurality of sound velocities at one point of the object.

2. The ultrasonic apparatus of claim 1, wherein the transducer is further configured to irradiate a second plurality of ultrasonic waves which travel in different directions within a single plane toward the object, and
wherein the controller is further configured to acquire a second plurality of respective sound velocities of the second plurality of ultrasonic waves in the object and to compound the acquired second plurality of sound velocities of the second plurality of ultrasonic waves in order to determine a planar composite sound velocity in the object which corresponds to the single plane.

3. The ultrasonic apparatus of claim 1, wherein the transducer is further configured to irradiate, onto the object, a third plurality of ultrasonic waves which travel in different respective directions in a respective plurality of planes, and
wherein the controller is further configured to classify and acquire respective sound velocities of the third plurality of ultrasonic waves and to determine a spatial composite sound velocity in the object based on the classified and acquired sound velocities of the third plurality of ultrasonic waves.

4. The ultrasonic apparatus of claim 3, wherein the controller is further configured to compound the classified and acquired sound velocities of the third plurality of ultrasonic waves in order to determine a plurality of planar composite sound velocities in the object which respectively correspond to the plurality of planes, and to compound the determined plurality of planar composite sound velocities in order to determine the spatial composite sound velocity in the object.

5. The ultrasonic apparatus of claim 1, wherein the controller is further configured to acquire the first plurality of sound velocities of the first plurality of ultrasonic waves in the object by using a difference between a respective irradiation time of each of the first plurality of ultrasonic waves and a corresponding collection time of each of the first plurality of echo ultrasonic waves.

6. An ultrasonic apparatus comprising:
a transducer configured to irradiate a plurality of ultrasonic waves which have different respective traveling directions onto an object and to collect a plurality of echo ultrasonic waves reflected from the object;
a controller configured to acquire a plurality of respective sound velocities of the plurality of ultrasonic waves in the object and to compound the acquired plurality of sound velocities in order to determine a composite sound velocity in the object; and
a beamformer configured to delay the collected echo ultrasonic waves based on the determined composite sound velocity, to focus the delayed echo ultrasonic waves, and to convert the focused echo ultrasonic waves into respective ultrasonic image signals, wherein a first ultrasonic wave from among the plurality of ultrasonic waves originates from a first point and has a first traveling direction, and at least a second ultrasonic wave from among the plurality of ultrasonic waves originates from the first point and has a second traveling direction that is different from the first traveling direction, and wherein the controller is further configured to perform the compounding by acquiring one of a mean value, a median value, a root mean square value, a maximum value, and a minimum value of the first plurality of sound velocities at one point of the object.

7. An ultrasonic apparatus comprising:

a transducer configured to irradiate a plurality of ultrasonic waves which have different respective traveling directions onto an object and to collect a plurality of echo ultrasonic waves reflected from the object;

a controller configured to acquire a plurality of respective sound velocities of the plurality of ultrasonic waves in the object and to compound the acquired plurality of sound velocities in order to determine a composite sound velocity in the object; and a thermal image generator configured to generate a thermal image of the object based on the determined composite sound velocity, wherein a first ultrasonic wave from among the plurality of ultrasonic waves originates from a first point and has a first traveling direction, and at least a second ultrasonic wave from among the plurality of ultrasonic waves originates from the first point and has a second traveling direction that is different from the first traveling direction, and wherein the controller is further configured to perform the compounding by acquiring one of a mean value, a median value, a root mean square value, a maximum value, and a minimum value of the first plurality of sound velocities at one point of the object.

8. The ultrasonic apparatus of claim 7, further comprising a display configured to display the generated thermal image on a screen by using a respective plurality of different colors to represent a corresponding plurality of different temperatures.

9. A method for controlling an ultrasonic apparatus, the method comprising:

irradiating a plurality of ultrasonic waves which have different respective traveling directions onto an object;

collecting a plurality of echo ultrasonic waves reflected from the object;

acquiring a plurality of respective sound velocities of the plurality of ultrasonic waves in the object; and compounding the acquired plurality of sound velocities in order to determine a composite sound velocity in the object, wherein a first ultrasonic wave from among the plurality of ultrasonic waves originates from a first point and has a first traveling direction, and at least a second ultrasonic wave from among the plurality of ultrasonic waves originates from the first point and has a second traveling direction that is different from the first traveling direction, and wherein the compounding further comprises acquiring one of a mean value, a median value, a root mean square value, a maximum value, and a minimum value of the plurality of sound velocities at one point of the object.

10. The method of claim 9, wherein the irradiating comprises irradiating the plurality of ultrasonic waves which travel in different respective directions within a single plane toward the object, wherein the acquiring comprises acquiring the plurality of sound velocities of the plurality of ultrasonic waves in the object with respect to the single plane, and wherein the compounding comprises compounding the plurality of sound velocities in order to determine a planar composite sound velocity in the object which corresponds to the single plane.

11. The method of claim 9, wherein the irradiating comprises irradiating the plurality of ultrasonic waves which travel in different respective directions in a respective plurality of planes toward the object, wherein the acquiring comprises classifying and acquiring respective sound velocities of the plurality of ultrasonic waves with respect to each of the plurality of planes, and wherein the compounding comprises determining a spatial composite sound velocity in the object based on the classified and acquired sound velocities of the plurality of ultrasonic waves.

12. The method of claim 11, wherein the compounding comprises compounding the classified and acquired sound velocities of the plurality of ultrasonic waves in order to determine a plurality of planar composite sound velocities in the object which respectively correspond to the plurality of planes, and compounding the determined plurality of planar composite sound velocities in order to determine a spatial composite sound velocity in the object.

13. The method of claim 9, wherein the irradiating comprises acquiring the plurality of sound velocities of the plurality of ultrasonic waves in the object by using a difference between a respective irradiation time of each of the plurality of ultrasonic waves and a corresponding collection time of each of the plurality of echo ultrasonic waves.

14. A method for controlling an ultrasonic apparatus, the method comprising:

irradiating a plurality of ultrasonic waves which have different respective traveling directions onto an object;

collecting a plurality of echo ultrasonic waves reflected from the object;

acquiring a plurality of respective sound velocities of the plurality of ultrasonic waves;

compounding the plurality of sound velocities in order to determine a composite sound velocity in the object; and delaying the collected echo ultrasonic waves based on the determined composite sound velocity, focusing the delayed echo ultrasonic waves, and converting the focused echo ultrasonic waves into respective ultrasonic image signals, wherein a first ultrasonic wave from among the plurality of ultrasonic waves originates from a first point and has a first traveling direction, and at least a second ultrasonic wave from among the plurality of ultrasonic waves originates from the first point and has a second traveling direction that is different from the first traveling direction, and wherein the compounding further comprises acquiring one of a mean value, a median value, a root mean square value, a maximum value, and a minimum value of the plurality of sound velocities at one point of the object.

15. A method for controlling an ultrasonic apparatus, the method comprising:

irradiating a plurality of ultrasonic waves which have different respective traveling directions onto an object;

acquiring a plurality of respective sound velocities of the plurality of ultrasonic waves;

compounding the plurality of sound velocities in order to determine a composite sound velocity in the object; and generating a thermal image of the object based on the determined composite sound velocity, wherein a first ultrasonic wave from among the plurality of ultrasonic waves originates from a first point and has a first traveling direction, and at least a second ultrasonic wave from among the plurality of ultrasonic waves originates from the first point and has a second traveling direction that is different from the first traveling direction, and wherein the compounding further comprises acquiring one of a mean value, a median value, a root mean square value, a maximum value, and a minimum value of the plurality of sound velocities at one point of the object.

16. The method of claim 15, further comprising displaying the generated thermal image on a screen by using a respective plurality of different colors to represent a corresponding plurality of different temperatures.

17. The ultrasonic apparatus of claim 1, wherein a third ultrasonic wave from among the first plurality of ultrasonic waves originates from the first point and has a third traveling direction that is different from each of the first traveling direction and the second traveling direction.

* * * * *